United States Patent [19]

Shiratsuchi et al.

[11] Patent Number: 4,727,085
[45] Date of Patent: Feb. 23, 1988

[54] RACEMATES OF 3,4-DIHYDRO-8-(2'-HYDROXY-3'-ISO-PROPYLAMINO)PROPOXY-3-NITROXY-2H-1-BENZOPYRAN, PROCESS FOR CONVERTING THEM AND PHARMACEUTICAL COMPOSITIONS THEREOF

[75] Inventors: Masami Shiratsuchi, Musashimurayama; Kiyoshi Kawamura, Tokorozawa; Toshihiro Akashi; Hiroshi Ishihama, both of Higashimurayama; Yasumi Uchida, Ichikawa, all of Japan

[73] Assignee: Kowa Company, Ltd., Nagoya, Japan

[21] Appl. No.: 706,748

[22] Filed: Feb. 28, 1985

[30] Foreign Application Priority Data

Feb. 29, 1984 [JP] Japan .................. 59-36178

[51] Int. Cl.$^4$ .................. A61K 31/35; C07C 311/64
[52] U.S. Cl. ........................ 514/456; 549/399
[58] Field of Search .................. 549/399; 514/456

[56] References Cited

U.S. PATENT DOCUMENTS 4,394,382 7/1983 Shiratsuchi et al. .............. 549/399

FOREIGN PATENT DOCUMENTS 42299 12/1981 European Pat. Off. .
7481 6/1980 Japan .
106619 12/1980 Japan .

*Primary Examiner*—Nicky Chan
*Attorney, Agent, or Firm*—Wenderoth, Lind & Ponack

[57] ABSTRACT

A novel racemate K-351A composed of an optical isomer (2'S),(3S)K-351 [3,4-dihydro-8-(2'-hydroxy-3'-isopropylamino)propoxy-3-nitroxy-2H-1-benzopyran] and (2'R),(3R)K-351, a novel racemate K-351B composed of an optical isomer (2'R),(3S)K-351 and (2'S),(3R)K351 and an acid addition salt of these two novel racemates; a process for converting the two racemates to each other; and also to a pharmaceutical composition comprising each of the two racemates useful for the treatment of cardiovascular diseases.

5 Claims, No Drawings

RACEMATES OF 3,4-DIHYDRO-8-(2'-HYDROXY-3'-ISO-PROPYLAMINO)PROPOXY-3-NITROXY-2H-1-BENZOPYRAN, PROCESS FOR CONVERTING THEM AND PHARMACEUTICAL COMPOSITIONS THEREOF

This invention relates to two racemates of 3,4-dihydro-8-(2'-hydroxy-3'-isopropylamino)propoxy-3-nitroxy-2H-1-benzopyran (to be abbreviated K-351 in this invention), acid addition salts of these racemates, a process for converting the two racemates to each other, and also to a pharmaceutical composition comprising each of the two racemates.

K-351 is a known compound represented by the following formula

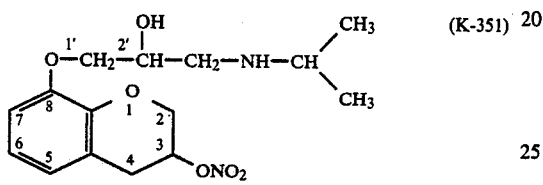

It is useful as a drug for the cardiovascular diseases having beta-blocking activity and vasodilating activity (direct vasodilating activity and alpha-blocking activity) (Japanese Laid-Open Patent Publications Nos. 7481/1982 and 106619/1982, and corresponding U.S. Pat. No. 4,394,382 and European Laid-Open Patent Publication No. 42299).

Since K-351 has asymmetric carbon atoms at the 3-position of the benzopyran ring and the 2'-position of the side chain, two racemates, i.e. 4 optical isomers, can exist theoretically. However, no mention has previously been made on the racemates or optical isomers of K-351, and no method for their separation or resolution has been known.

The present inventors have studied the optical isomers of K-351 and their pharmacological activities, and have found that K-351 can be easily separated into two racemates, and the separated two racemates exhibit different pharmacological activities. The inventors have further discovered that by selectively administering one of the racemates to a patient according to his condition, the trouble of side effects can be reduced, and a therapeutic effect can be obtained efficiently.

Investigations of the present inventors have shown that separation of K-351 by, for example, recrystallization gives two kinds of crystals, i.e. a racemate having high crystallinity and a racemate having low crystallinity. A high-performance liquid chromatographic study of derivatives of these racemates has shown that the racemate having high crystallinity is a racemate (to be referred to as racemate K-351A in this invention) composed of an optical isomer(2'S),(3S) K-351 of the following formula (A-1) and an optical isomer (2'R),(3R) K-351 of the following formula (A-2), and that the racemate having low crystallinity is a racemate (to be referred to as racemate K-351B in this invention) composed of an optical isomer (2'R),(3S) K-351 and an optical isomer (2'S),(3R) K-351 of the following formula (B-2).

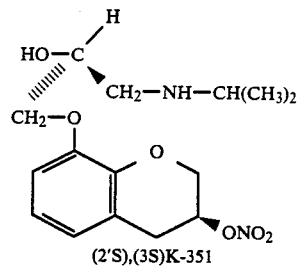

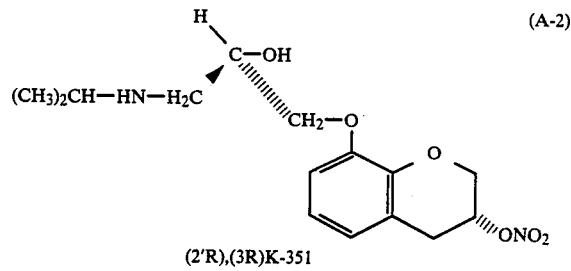

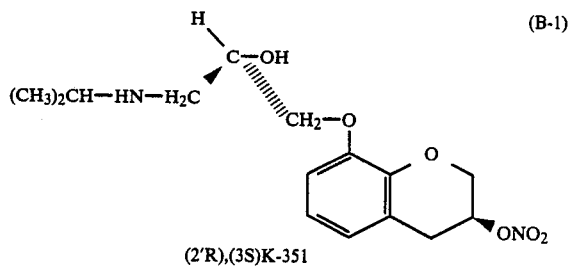

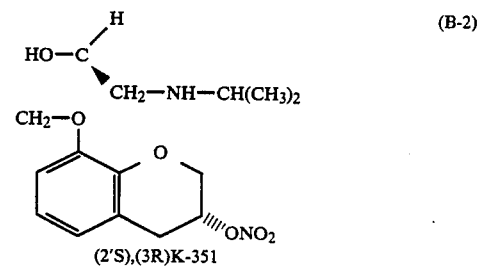

The investigations of the present inventors have also shown that the racemate K-351A shows toxicity, vasodilating activity and hypotensive activity nearly equivalent to those of K-351 but its beta-blocking activity is about one-tenth of that of K-351, and that the racemate K-351B has toxicity, vasodilating activity and hypotensive activity nearly equivalent to those of K-351 but its beta-blocking activity is about 2 times as strong as that of K-351. The racemate K-351A has been found to be useful as drugs for cardiovascular diseases such as an agent for treating the hypertension of patients who have a tendency to cardiac failure, bradycardia, etc., an agent for treating angina pectoris with a spasm of the coronary artery, and an agent for treating myocardial infarction. The racemate K-351B has been found to be useful as drugs for cardiovascular diseases such as a hypotensive agent and an antiarrhythmic agent.

It has been found therefore that by separating K-351 into these two racemates K-351A and K-351B and administering one of the racemates according to the condition of a patient, the patient can be treated efficiently with reduced manifestation of side-effects.

A method of obtaining one of the racemates K-351A and K-351B by separating K-351 into the two racemates and purifying them cannot give the desired one racemate in quantities, and is also disadvantageous in regard to industrial operations and cost. Further investigations of the inventors made in order to overcome this disadvantage have led to the finding an industrially advantageous process for converting the racemate K-351A into the racemate K-351B or vice versa.

It is an object of this invention therefore to provide novel racemate K-351A and a novel racemate K-351B, and acid addition salts of these racemates.

Another object of this invention is to provide a pharmaceutical composition comprising the novel racemate K-351A, or the novel racemate K-351B or a pharmaceutically acceptable acid addition salt thereof as an active ingredient.

Still another object of this invention is to provide a process for converting one of the racemates K-351A and 351B into the other.

The above and other objects and advantages of this invention will become more apparent from the following description.

According to this invention, there is provided a racemate selected from the group consisting of a racemate K-351A composed of an optical isomer (2'S),(3S) K-351 of the following formula (A-1) and an optical isomer (2'R),(3R) K-351 of the following formula (A-2)

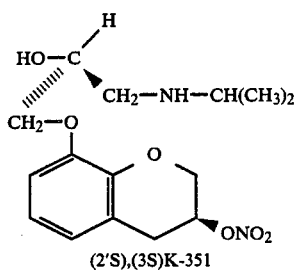

(2'S),(3S)K-351

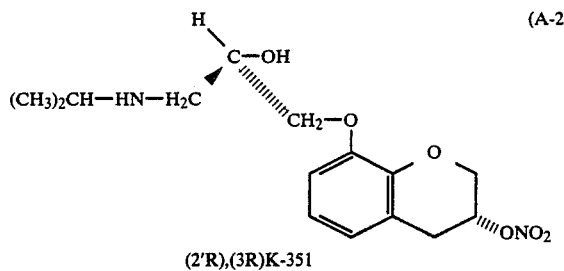

(2'R),(3R)K-351 and a racemate K-351B composed of an optical isomer (2'R),(3S) K-351 of the following formula (B-1) and an optical isomer (2'S),(3R) K-351 of the following formula (B-2)

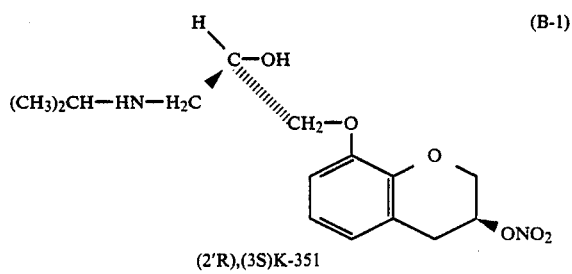

(2'R),(3S)K-351

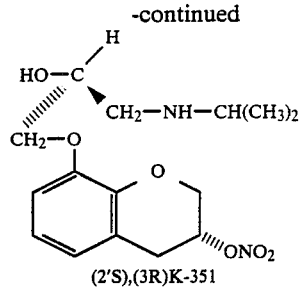

(2'S),(3R)K-351 and acid addition salts thereof.

According to this invention, there is also provided a process for converting one of the racemates of 3,4-dihydro-8-(2'-hydroxy-3'-isopropylamino)propoxy-3-nitroxy-2H-1-benzopyran (K-351) into the other, namely the racemate K-351A into the racemate K-351B or vice versa, which comprises reacting said one racemate with a compound represented by the following formula (I)

R—COOH (I)

wherein R represents an alkyl, cycloalkyl, aryl or aralkyl group, or its reactive derivative to form a compound represented by the following formula (II)

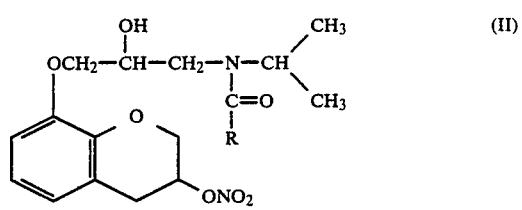

wherein R is as defined above, reacting the resulting compound with an inversion reagent to form an oxazolinium ion represented by the following formula (III)

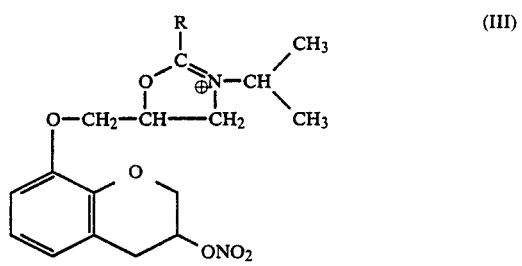

wherein R is as defined above, allowing an acid to act on the oxazolinium ion and then hydrolyzing it. The starting racemate K-351A or K-351B can be separated from K-351 by using a recrystallizing method, for example, as described in detail hereinafter.

Application of the above process to the racemate K-351A can effect conversion of (2'S),(3S) K-351 into (2'R),(3S) K-351, and (2'R),(3R) K-351 into (2'S),(3R) K-351. Application of the above process to the racemate K-351B can effect conversion of (2'R),(3S) K-351 into (2'S),(3S) K-351, and (2'S),(3R) K-351 into (2'R),(3R) K-351.

According to the above conversion process, all the racemates can be industrially used in good yields by converting one of the racemates into the other desired racemate. To convert the racemates, it is sufficient only to change the arrangement of one of the 2'-position of the side chain and the 3-position of the benzopyran ring of one of the racemates. According to the process of this invention, the objective can be achieved by acylating the side-chain amino group of one of the racemates with the compound of formula (I) or its reactive derivative to form the compound of formula (II), allowing an inversion reagent to act on the compound of formula (II) to form an oxazole ring and form an oxazlinium ion of formula (III), allowing an acid to act on it to cleave the ring and thereby changing the arrangement of the hydroxyl group, and thereafter or simultaneously hydrolyzing the oxazolinium ion, whereby the arrangement of the side-chain 2'-position is converted.

The conversion of (2'S) K-351 into (2'R) K-351 by the process of this invention can be schematically shown as follows. R in these formulae is as defined hereinabove.

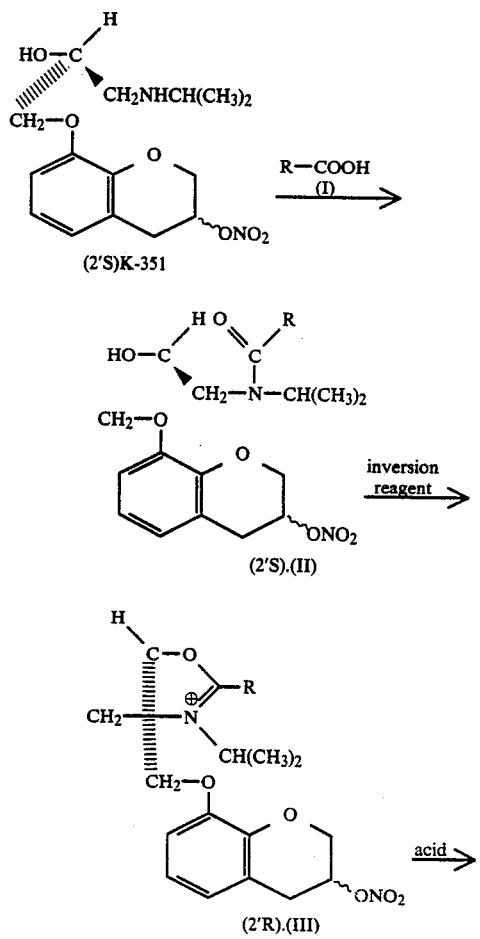

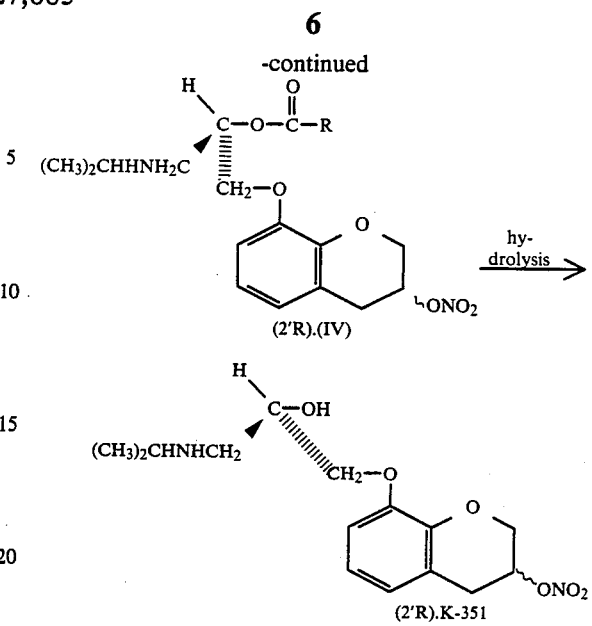

The individual steps of the conversion process of this invention will be described below in detail.

(1) Separation of the racemates K-351A and K-351B from K-351 and their purification The free base of K-351 is separated into two racemates by recrystallization. A racemate having high crystallinity after recrystallization is racemate K-351A, and a racemate having low crystallinity after recrystallization is racemate K-351B. Recrystallization solvents that can be used for this purpose include, for example, ethyl acetate, methanol, ethanol, isopropanol, acetone, benzene, toluene, chloroform, and tetrahydrofuran.

The crystallization can be performed by known recrystallization techniques. For example, K-351 is dissolved in a solvent such as ethyl acetate, and the first crystals are collected. Recrystallization of the first crystals several times from the same solvent can give the racemate K-351A as a nearly pure product. The mother liquor left after collection of the first crystals is concentrated to dryness and an acid such as oxalic acid, acetic acid, fumaric acid and maleic acid is allowed to act on it to form an acid addition salt. The salt is recrystallized several times from a solvent such as methanol, ethanol, isopropanol and water either singly or in combination, and then converted to a free base in a customary manner. Recrystallization of the free base from the aforesaid solvents can give pure racemate K-351B.

(2) Reaction of the racemate K-351A (or K-351B) with a carboxylic acid of the following formula

R—COOH  (I)

wherein R is as defined hereinabove, or its reactive derivative gives a compound of formula (II) with the acylation of the side-chain amino group.

Examples of the alkyl group for the substituent R of the carboxylic acid of formula (I) are linear or branched alkyl groups having 1 to 5 carbon atoms such as methyl, ethyl, tert.-butyl and tert.-amyl groups. A cyclohexyl group is an example of the cycloalkyl group for R. Examples of the aryl group for R are aryl groups having 6 to 10 carbon atoms such as phenyl, p-(or o-)nitrophenyl and naphthyl groups. Examples of the aralkyl group for R are phenyl-lower alkyl groups which may have a substituent, such as benzyl and p-methoxybenzyl group. Examples of the reactive derivatives of the carboxylic acid of formula (I) are acid halides such as acid chlorides and bromides, azides, acid anhydrides, mixed acid anhydrides, and active esters such as phenyl, cyanomethyl, N-hydroxysuccinimide, and N-hydroxyphthalimide esters.

The reaction is carried out preferably in a solvent in the presence of a dehydrating or condensing agent. N,N-dicyclohexylcarbodiimide, for example, can be used as the dehydrating agent. Examples of the condensing agent include chloroformates; and phosphite esters such as diesters of chlorophosphorous acid, monoesters of dichlorophosphorous acid and tetraethyl pyrophosphite. Examples of the solvent are chloroform, tetrahydrofuran, benzene, methylene chloride and mixtures thereof.

The reaction temperature and time can be properly selected and changed. For example, the reaction may be carried out at a temperature of about −50° to about 100° C. for a period of about 1 to about 50 hours.

The separation and purification of the reaction product can be carried out in a customary manner, for example by solvent extraction or chromatography. Depending upon the reaction conditions, a by-product compound may be formed by the simultaneous esterification of the hydroxyl group at the 2'-position of the side chain with the carboxylic acid of formula (I). Separation of this compound from the desired compound can be carried out easily, for example, by silica gel column chromatography.

(3) The reaction of the inversion reagent upon the compound of formula (II) results in the formation of an oxazole ring, and an oxazolinium ion of formula (III) is obtained.

Examples of the inversion reagent include thionyl chloride, p-toluenesulfonyl chloride, benzenesulfonyl chloride, o-(or p-)nitrobenzenesulfonyl chloride, phosphorus trichloride, phosphorus tribromide and phosphorus oxychloride. The reaction can be carried out by allowing the inversion reagent to act on the compound of formula (II) at about 0° to about 100° C. for about 1 to about 100 hours in the presence or absence of a solvent. The solvent may be the same as exemplified hereinabove in section (2). The inversion reagent may be used in excess to cause it to serve concurrently as solvent. The separation and purification of the reaction product (III) can be carried out in a customary manner, for example by solvent extraction or chromatography. The crude product may be used as a starting material for the next step whithout particularly purifying it.

(4) The action of an acid on the compound (III) causes cleavage of the ring, and the ester of K-351 represented by formula (IV) is obtained.

The acid may be an inorganic acid such as hydrochloric acid, sulfuric acid, nitric acid and phosphoric acid, or an organic acid such as acetic acid. The reaction is carried out, for example, in a solvent at about 0° to to about 100° C., and is completed, for example, in about 1 to about 30 hours. The solvent may be the same as exemplified in section (2) above. The separation and purification of the reaction product can be carried out in a customary manner, for example by solvent extraction or chromatography. It may also be used directly in the subsequent reaction without purification.

(5) When the compound of formula (IV) is subsequently hydrolyzed to remove the acyl group, the desired racemate K-351B (or K-351A) with the change of the arrangement of the side chain 2'-position can be obtained. The hydrolysis can be carried out by using acids or alkalies. Alkaline hydrolysis is preferred. An alkali hydroxide such as sodium hydroxide and potassium hydroxide is preferably used as the alkali. The reaction is carried out in the aforesaid solvent at a temperature of, for example, about 0° to about 100° C. for several minutes to about 20 hours. The separation and purification of the reaction product can be carried out in a customary manner, for example by solvent extraction or chromatography.

The racemate K-351A is useful as a hypotensive agent having vasodilating action and as agents for treating angina pectoris, myocardial infarction, cardiac failure, etc. The racemate K-351B is useful as a hypotensive agent having beta-blocking action and as an antiarrhythmic agent. These racemates may be used as agents for treating cardiovascular diseases in the form of free bases or physiologically acceptable acid addition salts such as salts with hydrochloric acid, sulfuric acid, acetic acid, lactic acid, oxalic acid, maleic acid and p-toluenesulfonic acid.

Thus, according to this invention, there is provided a pharmaceutical composition comprising (1) an amount, effective for the treatment of cardiovascular diseases, of a racemate K-351A composed of an optical isomer (2'S),(3S) K-351 of the following formula (A-1) and an optical isomer (2'R),(3R) K-351 of the following formula (A-2)

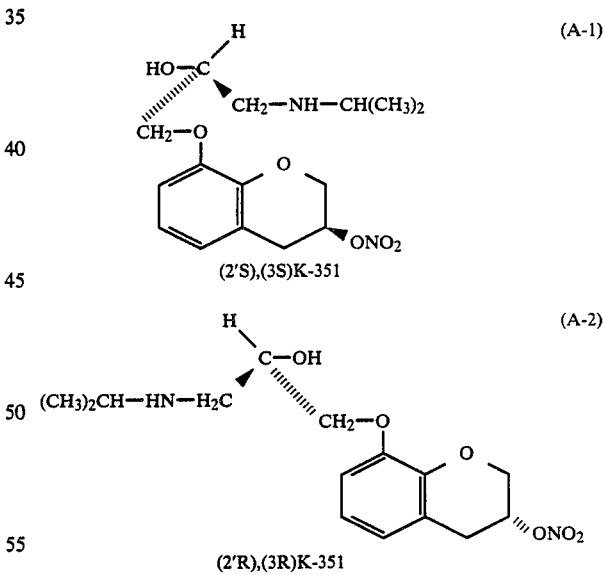

or a pharmaceutically acceptable acid addition salt thereof, and (2) a pharmaceutically acceptable diluent or carrier.

According to this invention, there is also provided a pharmaceutical composition comprising (1) an amount, effective for the treatment of cardiovascular diseases, of a racemate K-351B composed of an optical isomer (2'R),(3S) K-351 of the following formula (B-1) and an optical isomer (2'S),(3R) K-351 of the following formula (B-2)

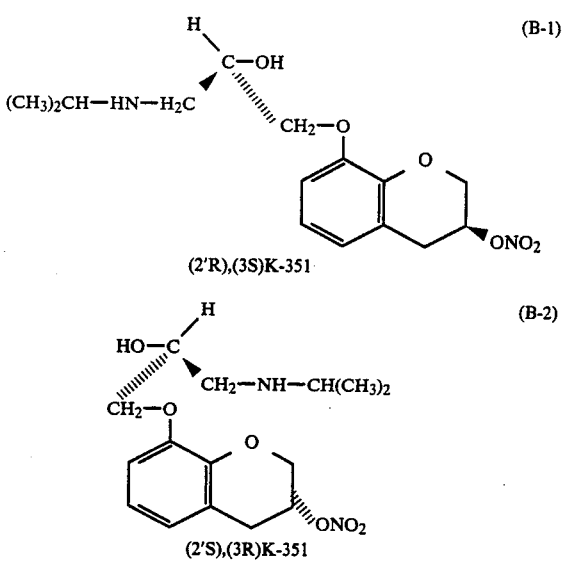

(B-1) (2'R),(3S)K-351

(B-2) (2'S),(3R)K-351 or a pharmaceutically acceptable acid addition salt thereof and (2) a pharmaceutically acceptable diluent or carrier.

In the above pharmaceutical compositions, the amount of the racemate K-351A or K-351B or an acid addition salt thereof is, for example, about 0.01 to about 99% by weight based on the total weight of the pharmaceutical composition.

Liquid or solid carriers or diluents may be used in formulating the pharmaceutical composition of this invention. They may include excipients, binders, lubricants, emulsifiers, etc. known in pharmaceutical production. Examples of these carriers or diluents include starches such as potato starch, wheat starch, corn starch and rice starch; sugars such as lactose, sucrose, glucose, mannitol and sorbitol; celluloses such as crystalline cellulose, calcium carboxymethyl cellulose and hydroxypropyl cellulose of a low degree of substitution; inorganic substances such as potassium phosphate, calcium sulfate, calcium carbonate and talc; binder compounds such as gelatin, gum arabic, methyl cellulose, sodium carboxymethyl cellulose, polyvinyl pyrrolidone and hydroxypropyl cellulose; polyhydric alcohol ester-type nonionic surfactants such as fatty acid monoglycerides, sorbitan fatty acid esters, sucrose and polyglycerol fatty acid esters; and polyoxyethylene-type nonionic surfactants.

The pharmaceutical compositions may be in any dosage forms known in the art of formulating pharmaceuticals, such as suppositories, powders, granules, tablets, sublingual tablets, liquid preparations, injectable preparations and suspension.

The pharmaceutical compositions of this invention may be administered through any of peroral and parenteral routes, such as intravenous, sublingual or intrarectal administration. For long-term administration, the oral route is preferred.

The dose may be changed as desired. For example, the racemate K-351A or racemate K-351B may be administered in a dose of about 1 to about 100 mg/body/day, preferably about 5 to about 50 mg/body/day. The compounds of this invention have low toxicity as shown by their acute toxicity ($LD_{50}$).

Some examples are given below for testing the pharmacological efficacy of the compounds in accordance with this invention.

EXPERIMENTAL EXAMPLE 1

Acute toxicity:

Racemate K-351A, racemate K-351B, and K-351 were each subjected to an acute toxicity test using mice and rats, and the $LD_{50}$ values of these compounds were determined. The resutls are shown in Table 1.

TABLE 1

| Compound tested | $LD_{50}$ (mg/kg) | | |
|---|---|---|---|
| | Mouse | | Rat |
| | Intravenous | Oral | Intravenous |
| Racemate K-351A | 86.0 | 490 | 68.0 |
| Racemate K-351B | 84.0 | 540 | 66.0 |
| K-351 | 74.0 | 540 | 73.0 |

The results in Table 1 show no clear difference in acute toxicity $LD_{50}$ value among racemate K-351A, racemate K-351B, and K-351.

EXPERIMENTAL EXAMPLE 2 beta-Blocking activity:

Racemate K-351A, racemate K-351B, and K-351 were each tested for their antagonistic acition on isoproterenol, i.e. their beta-blocking action, using isolated atrium and trachea of guinea pigs. The results are shown in Table 2. In the table, $pA_2$ shows the reciprocal logarithm of the molar concentration of each test compound required to shift the dose-response curve of isoproterenol parallel toward a higher dose side by 2 times.

TABLE 2

| Compound tested | $pA_2$ | | |
|---|---|---|---|
| | Atrium | | |
| | Heart rate | Contracting force | Trachea |
| Racemate K-351A | 7.60 | 8.00 | 7.35 |
| Racemate K-351B | 9.00 | 9.00 | 8.54 |
| K-351 | 8.92 | 8.72 | 8.33 |

The results show that the beta-blocking activity of racemate K-351A is about one-tenth of that of K-351, and the beta-blocking activity of racemate K-351B is about twice that of K-351.

EXPERIMENTAL EXAMPLE 3

Vasodilating activity:

Racemate K-351A, racemate K-351B, and K-351 were each tested for their antagonistic action on potassium contracture (direct vaso-relaxing activity) and their antagonistic action on the contractile activity of norepinephrine (NE) (alpha-blocking activity) using the isolated superior mesenteric artery of dogs. The results are shown in Table 3.

In the table $pD_2$ represents the reciprocal logarithm of the molar concentration of each test compound required to inhibit the maximum reaction of potassium (25 m MK+) by an extent of 50%; and $pA_2$ represents the reciprocal logarithm of the molar concentration of each test compound required to shift the dose-response curve of norepinephrine parallel toward a high dose side by 2 times.

TABLE 3

| Compound tested | K+ contracture [pD₂] | NE contraction [pA₂] |
|---|---|---|
| Racemate K-351A | 6.18 ± 0.06 | 6.31 ± 0.10 |
| Racemate K-351B | 6.10 ± 0.08 | 6.52 ± 0.05 |
| K-351 | 6.14 ± 0.05 | 6.43 ± 0.16 |

The results given in Table 3 demonstrate that there is hardly any difference in vasodilating activity among racemate K-351A, racemate K-351B, and K-351.

EXPERIMENTAL EXAMPLE 4

The hypotensive actions of racemate K-351A, racemate K-351B and K-351 were examined on spontaneously hypertensive rats which were conscious and unrestrained. Changes with time of the systolic blood pressure (SBP), diastolic blood pressure (DBP) and heart rate (HR) of the animals were determined, when each of the compounds was administered once (10 mg/kg po) and the results are shown in Table 4.

It is seen that racemate K-351B has a slightly stronger hypotensive activity than racemate K-351A, and K-351 shows a hypotensive activity of a degree intermediate between them. However, no essential difference in hypotensive activity is considered to exist among the three compounds tested.

TABLE 4

| Test item | Compound tested | 1 hour | 3 hours | 6 hours | 10 hours |
|---|---|---|---|---|---|
| ΔSBP (mm/Hg) | Racemate K-351A | −9.2 ± 5.5 | −12.8 ± 3.0 | −15.7 ± 2.6 | −13.3 ± 4.3 |
| | Racemate K-351B | −18.8 ± 4.2 | −24.2 ± 4.6 | −22.0 ± 2.8 | −14.2 ± 2.5 |
| | K-351 | −18.6 ± 3.5 | −20.7 ± 1.9 | −24.0 ± 2.1 | −17.4 ± 1.5 |
| ΔDBP (mm/Hg) | Racemate K-351A | −8.5 ± 4.2 | −10.8 ± 2.9 | −11.0 ± 1.8 | −8.7 ± 4.5 |
| | Racemate K-351B | −15.8 ± 4.4 | −21.5 ± 4.0 | −16.3 ± 1.9 | −10.5 ± 2.2 |
| | K-351 | −15.5 ± 3.4 | −17.8 ± 1.4 | −20.5 ± 1.8 | −14.2 ± 1.9 |
| ΔHR (beats/min.) | Racemate K-351A | −10.3 ± 7.1 | +2.0 ± 5.9 | +5.8 ± 3.2 | −1.2 ± 6.1 |
| | Racemate K-351B | −33.2 ± 8.9 | −22.8 ± 6.0 | −25.7 ± 5.4 | −17.2 ± 5.4 |
| | K-351 | −14.6 ± 3.7 | −3.0 ± 4.2 | −7.2 ± 4.0 | −6.3 ± 4.2 |

The following Examples illustrate the present invention more specifically.

EXAMPLE 1

Separation of racemate K-351A and racemate K-351B:

Recrystallization of 100 g of K-351 from 500 ml of ethyl acetate gave 70 g of the first crystals. Recrystallization of 70 g of the first crystals from ethyl acetate gave 46 g of the first crystals. The same operation was further repeated twice to give 30 g of racemate K-351A having a purity of 98% as colorless needles having a melting point of 138° to 140° C.

NMR value: δCDCl₃, ppm
1.08 (6H, d, J=6Hz)

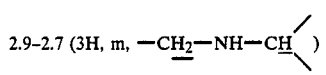

2.9–2.7 (3H, m, —CH₂—NH—CH )

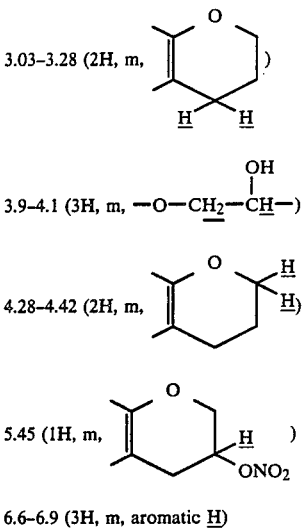

3.03–3.28 (2H, m, )

3.9–4.1 (3H, m, —O—CH₂—CH—)

4.28–4.42 (2H, m, )

5.45 (1H, m, )

6.6–6.9 (3H, m, aromatic H)

IR value: $\nu_{max}^{KBR}$, cm⁻¹: 3274 (NH), 3115 (OH), 1620, 1279 (NO₂).

High-performance liquid chromatography: Measured by using the di-p-nitrobenzoate of the racemic mixture.

Hold time: 15.2 minutes
Column: Partisil-10
Solvent: hexane-ethyl acetate (8:5)
Flow rate: 0.8 ml/min.

The initial mother liquor left after separation of racemate K-351A was concentrated to dryness and dissolved in methanol and 45 g of oxalic acid was added. The resulting crude oxalate salt was recrystallized four times from methanol to give racemate K-351B oxalate having a melting point of 179° to 181° C.

The oxalate was dissolved in a saturated aqueous solution of sodium hydrogen carbonate, and extracted and recrystallized from ethyl acetate to give 17.1 g of racemate K-351B having a purity of about 98% as colorless needles having a melting point of 118° to 119° C.

High-performance liquid chromatography: Measured under the same conditions as above using the same derivative as above.

Retention time: 12 minutes

The NMR and IR values of this product agreed with those of racemate K-351A given above.

Conversion of racemate K-351A to racemate K-351B:

(a) 1.640 g of K-351A obtained above was dissolved in 15 ml of pyridine, and 1.02 g of p-nitrobenzoyl chloride was added. The mixture was stirred overnight at room temperature. To the reaction mixture was added 100 ml of ethyl acetate, and the mixture was washed successively with dilute hydrochloric acid, a dilute aqueous solution of sodium hydrogen carbonate and water. The solvents were evaporated. The residue was separated and purified by silica gel column chromatography [solvent: benzene-chloroform (3:2)]. From the first fraction, 1.047 g (yield 43.8%) of 3,4-dihydro-8-[2'-hydroxy-3'-(N-isopropyl-N-p-nitrobenzoyl)amino]-propoxy-3-nitroxy-2H-1-benzopyran as a yellowish brown viscous oil.

NMR value: $\delta CDCl_3$, ppm
1.25 (6H, d, J=6Hz, $CH_3$)
5.42–5.62 (1H, m, $C_3$—H)

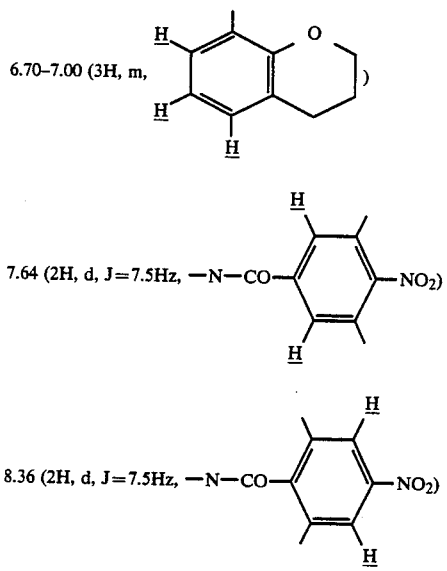

6.70–7.00 (3H, m, )

7.64 (2H, d, J=7.5Hz, —N—CO— —$NO_2$)

8.36 (2H, d, J=7.5Hz, —N—CO— —$NO_2$)

IR value: $\nu_{max}^{film}$, $cm^{-1}$: 1625 and 1275 ($ONO_2$).

(b) 325 mg of the resulting monobenzoate was added to 0.50 ml of cooled thionyl chloride, and the mixture was stirred for 3 hours at room temperature. Concentrating the reaction mixture gave a brown viscous oil. The oil was dissolved in 30 ml of ethanol, and 1 ml of 2N hydrochloric acid was added. The mixture was stirred overnight at room temperature. Concentrating the reaction mixture gave 450 mg of crude 3,4-dihydro-8-(3'-isopropylamino-2'-p-nitrobenzoyloxy)propoxy-3-nitroxy-2H-1-benzopyran hydrochloride as a brown viscous oil.

IR value: $\nu_{max}^{film}$, $cm^{-1}$

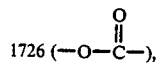

1726 (—O—C—), 1630 and 1278 ($ONO_2$)

(c) 450 mg of the resulting crude ester was dissolved in 10 ml of methanol, and 1 ml of a 4N aqueous solution of sodium hydroxide. The mixture was stirred for 3 hours at room temperature. The reaction mixture was acidified with dilute hydrochloric acid, and then concentrated. To the residue was added 200 ml of ethyl acetate, and the mixture was extracted with 40 ml of 2N hydrochloric acid. The extract was made basic by adding 2N sodium hydroxide, and then extracted with 50 ml of chloroform. The extract was washed with water, and then the solvent was evaporated. The residue was recrystallized with ethyl acetate/hexane to give 175 mg (yield 78.5% from mono-N-benzoate) of racemate K-351B as colorless needles having a melting point of 118° to 121° C.

The NMR and IR spectra of this product agreed with the spectra of the racemate K-351B obtained in Example 1. The high-performance liquid chromatogram of this product agreed with that of the derivative of racemate K-351B obtained in Example 1.

EXAMPLE 2

Conversion of racemate K-351B to racemate K-351A:

(a) 1.640 g of racemate K-351B obtained in Example 1 was treated in the same way as in Example 1, (a) to give 0.725 g (yield 30.3%) of the N-(p-nitro)benzamide of racemate K-351B as a yellowish brown viscous oil.

The NMR and IR values of the product agreed with those of the N-(p-nitro)benzamide of racemate K-351A.

(b) 480 mg of the resulting N-(p-nitro)benzamide was treated in the same way as in Example 1(b) and (c) to give 300 mg (yield 91.9%) of racemate K-351A as colorless needles having a melting point of 139° to 141° C.

This product agreed in NMR and IR spectra with racemate K-351B obtained in Example 1. The high-performance liquid chromatogram of this product determined by using its di-p-nitrobenzoate derivative agreed with that of the racemate K-351A derivative obtained in Example 1.

| FORMULATION EXAMPLE 1 | |
|---|---|
| Tablets: | |
| Racemate K-351A | 6 parts |
| Crystalline cellulose | 50 parts |
| Lactose | 34 parts |
| Carboxymethyl cellulose calcium | 9 parts |
| Magnesium stearate | 1 part |

The above ingredients were uniformly mixed and tableted into tablets each having a diameter of 5 mm and weighing 50 mg by a direct tableting method.

| FORMULATION EXAMPLE 2 | | |
|---|---|---|
| Granules: | | |
| (A) | Racemate K-351B | 1 part |
| | Crystalline cellulose | 25 parts |
| | Lactose | 40 parts |
| | Corn starch | 32 parts |
| (B) | Hydroxypropyl cellulose | 2 parts |
| | Ethanol | 25 parts |

The ingredients in (A) were uniformly mixed and then kneaded with the solution (B). The mixture was granulated by an extrusion method, dried in vacuum at 50° C., and sieved to form granules.

| FORMULATION EXAMPLE 3 | |
|---|---|
| Subtilized granules: | |
| Racemate K-351A | 2 parts |
| Crystalline cellulose | 20 parts |
| Lactose | 50 parts |
| Sucrose | 26 parts |

-continued

| FORMULATION EXAMPLE 3 | |
|---|---|
| Subtilized granules: | |
| Hydroxypropyl cellulose | 2 parts |

The above ingredients were uniformly mixed and by adding 25 parts of ethanol, kneaded. The mixture was granulated by a crushing method, then dried in vacuum at 50° C., and sieved to form subtilized granules.

| FORMULATION EXAMPLE 4 | |
|---|---|
| Capsules: | |
| Racemate K-351B | 10 parts |
| Lactose | 40 parts |
| Crystalline cellulose | 30 parts |
| Talc | 10 parts |

The above ingredients were uniformly mixed. 90 mg of the resulting mixture were filled in each of No. 5 lock capsules to form capsules.

What is claimed is:

1. A racemate selected from the group consisting of a racemate K-351A composed of an optical isomer (2'S),(3S) K-351 of the following formula (A-1) and an optical isomer (2'R),(3R) K-351 of the following formula (A-2)

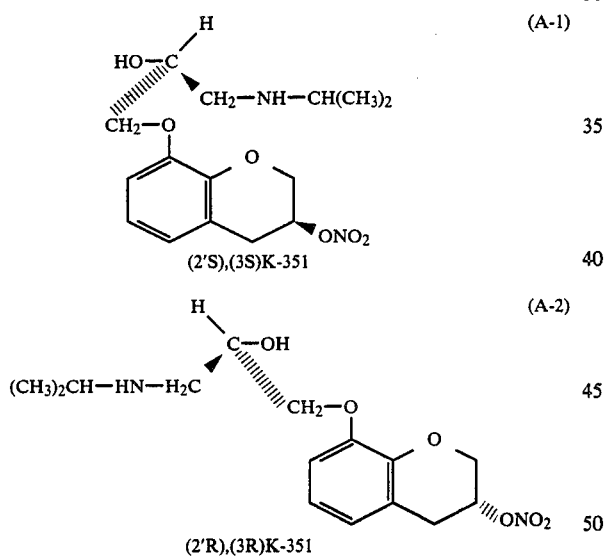

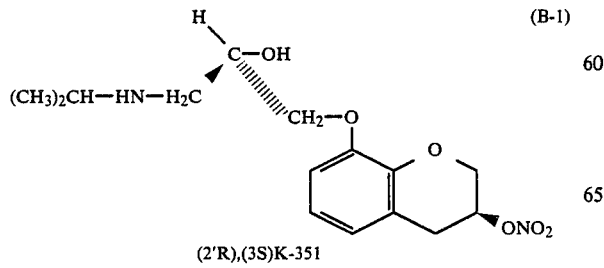

or a racemate K-351B composed of an optical isomer (2'R),(3S) K-351 of the following formula (B-1) and an optical isomer (2"S),(3R) K-351 of the following formula (B-2)

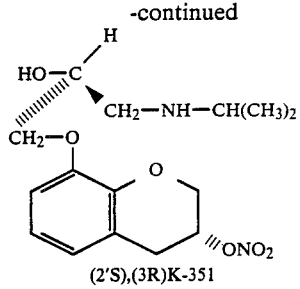

or pharmaceutically acceptable acid addition salts of these racemic mixtures.

2. A pharmaceutical composition comprising (1) an amount, effective for the treatment of cardiovascular diseases, of a racemate K-351A composed of an optical isomer (2'S),(3S) K-351 of the following formula (A-1) and an optical isomer (2'R),(3R) K-351 of the following formula (A-2)

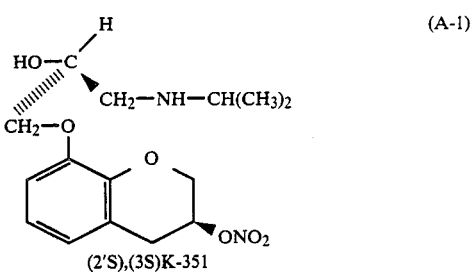

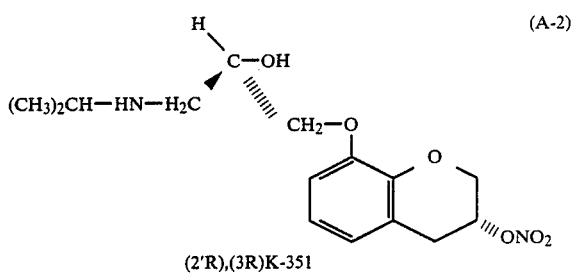

or a pharmaceutically acceptable acid addition salt thereof, and (2) a pharmaceutically acceptable diluent or carrier.

3. The pharmaceutical composition of claim 2 wherein the amount of the racemate K-351A or its acid addition salt is about 0.01 to about 99% by weight based on the total weight of the pharmaceutical composition.

4. A pharmaceutical composition comprising (1) an amount, effective for the treatment of cardiovascular diseases, of a racemate K-351B composed of an optical isomer (2'R),(3S) K-351 of the following formula (B-1) and and optical isomer (2'S),(3R) K-351 of the following formula (B-2)

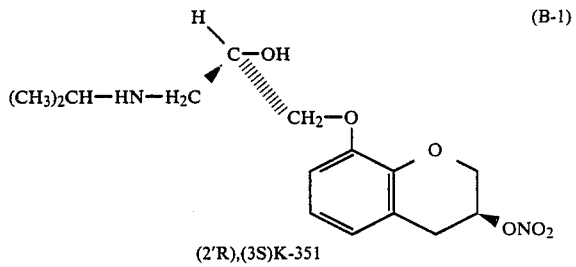

-continued
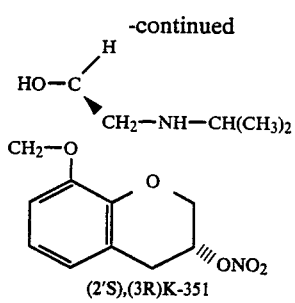
(2'S),(3R)K-351 (B-2)
or a pharmaceutically acceptable acid addition salt thereof and (2) a pharmaceutically acceptable diluent or carrier.
5. The pharmaceutical composition of claim 4 wherein the amount of the racemate 351B or its acid addition salt is about 0.01 to about 99% by weight based on the total weight of the pharmaceutical composition.
* * * * *

UNITED STATES PATENT AND TRADEMARK OFFICE
CERTIFICATE OF CORRECTION

PATENT NO. : 4,727,085

DATED : February 23, 1988

INVENTOR(S) : Masami SHIRATSUCHI, Kiyoshi KAWAMURA, Toshihiro AKASHI, Hiroshi ISHIHAMA, AND Yasumi UCHIDA It is certified that error appears in the above-identified patent and that said Letters Patent is hereby corrected as shown below:

Column 2, formula (B-2);

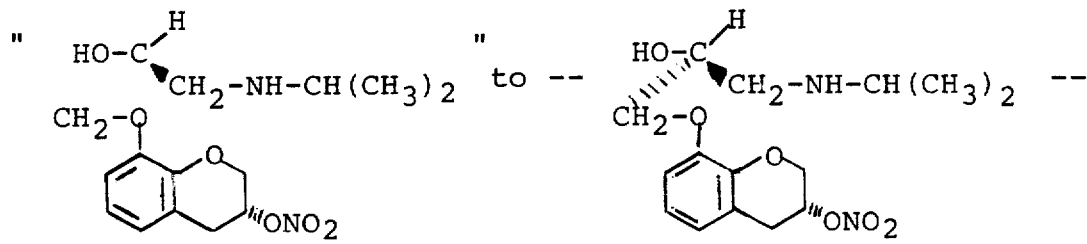

Column 5, formula (II);

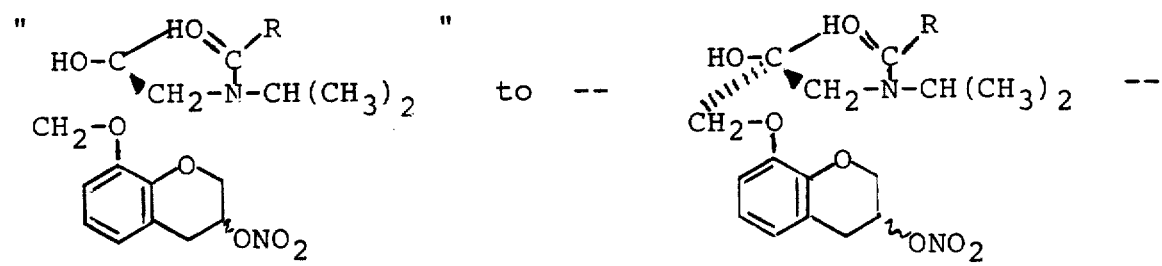

Column 5, formula (III);

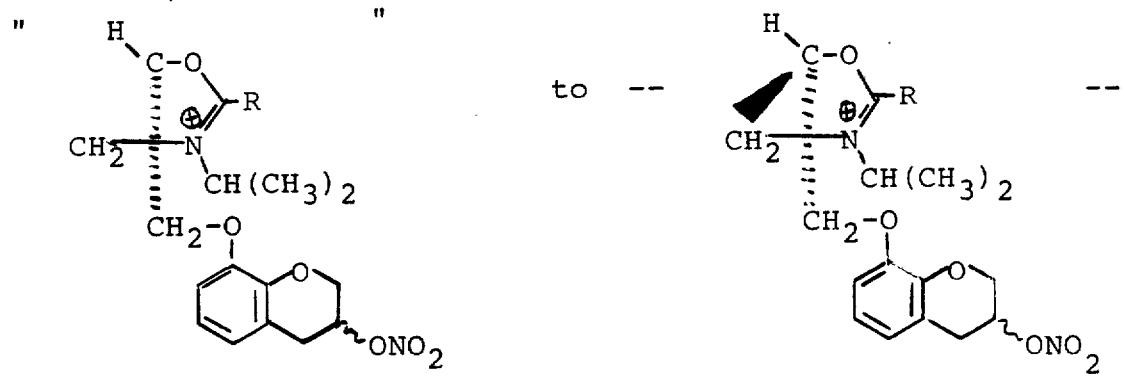

UNITED STATES PATENT AND TRADEMARK OFFICE
CERTIFICATE OF CORRECTION

PATENT NO. : 4,727,085
DATED : February 23, 1988
INVENTOR(S) : Masami SHIRATSUCHI, Kiyoshi KAWAMURA, Toshihiro AKASHI, Hiroshi ISHIHAMA, and Yasumi UCHIDA It is certified that error appears in the above-identified patent and that said Letters Patent is hereby corrected as shown below:

Column 15, line 55 (claim 1), change;

"(2"S),(3R) K-351" to -- (2'S),(3R) K-351 --

Column 17, formula (claim 4), change;

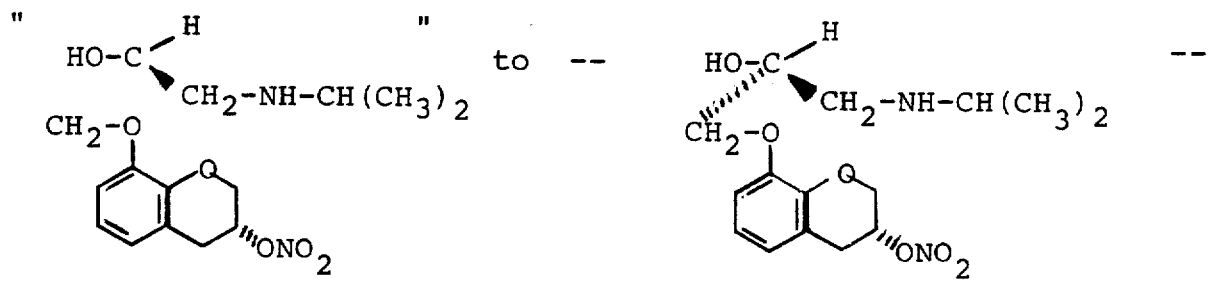

Column 18, line 8 (claim 5)
" racemate 351B " to -- racemate K-351B --.

Signed and Sealed this

Twenty-eighth Day of March, 1989

Attest:

DONALD J. QUIGG

Attesting Officer     Commissioner of Patents and Trademarks